United States Patent [19]

Yasuhara et al.

[11] Patent Number: 5,545,753
[45] Date of Patent: Aug. 13, 1996

[54] PROCESS FOR PREPARING ANILINES, CATALYSTS USED THEREFOR AND PROCESS FOR PREPARING SAME

[75] Inventors: Mitsuki Yasuhara; Yuuichirou Tatsuki; Mitsunori Nakamura; Fujihisa Matsunaga, all of Ichihara, Japan

[73] Assignee: Mitsui Petrochemical Industries, Ltd., Tokyo, Japan

[21] Appl. No.: 218,694

[22] Filed: Mar. 28, 1994

Related U.S. Application Data

[63] Continuation of Ser. No. 48,947, Apr. 12, 1993, which is a continuation of Ser. No. 660,269, Feb. 26, 1991, which is a continuation of Ser. No. 237,771, filed as PCT/JP87/00890, Nov. 17, 1987, published as WO88/03920, Jun. 2, 1988.

[30] Foreign Application Priority Data

Nov. 17, 1986 [JP] Japan ............................... 61-273497
Nov. 17, 1986 [JP] Japan ............................... 61-273498

[51] Int. Cl.$^6$ ............................................... C07C 85/06
[52] U.S. Cl. ....................................................... 564/402
[58] Field of Search ........................................... 564/402

[56] References Cited

U.S. PATENT DOCUMENTS

| | | | |
|---|---|---|---|
| 3,272,865 | 9/1966 | Barker | 564/402 |
| 3,860,650 | 1/1975 | Becker et al. | 564/402 |
| 4,326,080 | 4/1982 | Wedemeyer et al. | 564/402 |
| 4,380,669 | 4/1983 | Chang et al. | 564/402 |
| 4,400,537 | 8/1983 | Weil | 564/402 |
| 4,496,763 | 1/1985 | Le Blanc et al. | 564/402 |
| 5,001,156 | 3/1991 | Phillippe et al. | 514/887 |

*Primary Examiner*—Shelley A. Dodson
*Attorney, Agent, or Firm*—Sherman and Shalloway

[57] ABSTRACT

The process for preparing anilines by reaction of phenols with an amination agent in accordance with the present invention is disclosed, which process is characterized by carrying out the reaction of phenols with an amination agent in the presence of a low alkali and weakly acidic alumina catalyst having the alkali oxide content of less than 0.5% by weight, said alumina catalyst being obtained by firing an alumina catalyst containing in a dry state more than 80% by weight of alumina and less than 20% by weight of silica at a temperature of 600°–900° C., followed by acid treatment. According to the present invention, there are obtained such excellent effects that even when the reaction is carried out at a temperature lower than those employed in the case of conventionally well-known catalysts, the desired anilines can be prepared in high yields and high selectivity and, moreover, a high catalyst activity can be maintained over a long period of time.

The alumina catalyst used in the present invention is characterized by having the alkali metal oxide content of less than 0.5% by weight and pKa of from −3.0 to +6.8 as measured by Hammett's indicator, and containing in a dry state more than 80% by weight of alumina and less than 20% by weight of silica, and this catalyst is prepared by firing an alumina catalyst containing in a dry state more than 80% by weight of alumina and less than 20% by weight of silica at a temperature of 600°–900° C., followed by acid treatment.

14 Claims, 1 Drawing Sheet

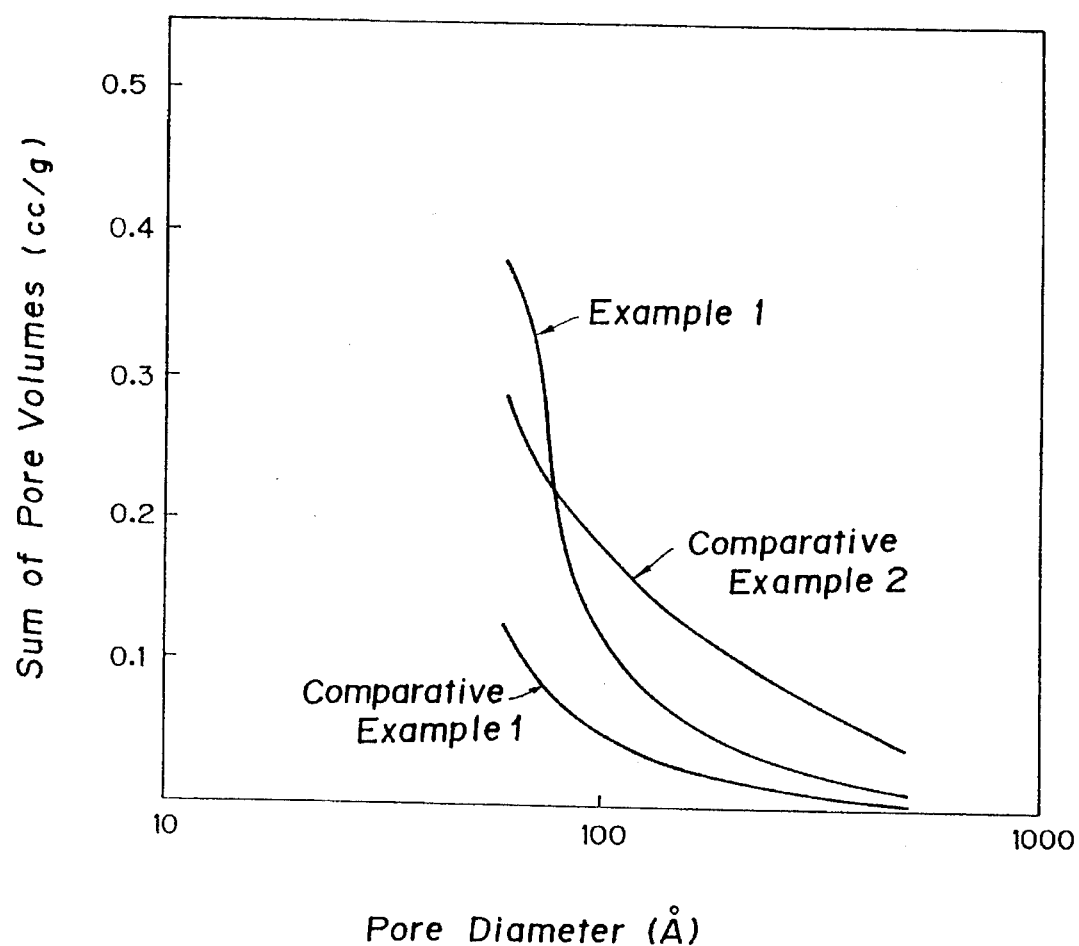

PROCESS FOR PREPARING ANILINES, CATALYSTS USED THEREFOR AND PROCESS FOR PREPARING SAME

This application is a continuation of application Ser. No. 08/048,947, filed Apr. 12, 1993; which is a continuation of Ser. No. 07/660,269, filed Feb. 26, 1991; which is a continuation of application Ser. No. 07/237,771, filed as PCT/JP87/00890, Nov. 17, 1987, published as WO88/03920, Jun. 2, 1988.

FIELD OF THE INVENTION

This invention relates to processes for preparing anilines, and more particularly to processes for preparing anilines in high yields by reacting phenols with amination agents in the presence of specific catalysts.

Furthermore, the present invention relates to alumina catalysts used in the above-mentioned processes for preparing anilines and to processes for preparing said catalysts.

BACKGROUND OF THE INVENTION

Anilines are important industrial chemicals of great commercial usefulness and are widely used in various fields of applications such as rubber vulcanization accelerators, antioxidants, dyes, intermediate dyes, etc., or starting materials for aniline resins. In recent years, moreover, new uses as starting materials for photographic chemicals, agricultural chemicals and medicines of aniline derivatives, for example, such compounds as toluidine, cumidine, methyl cumidine, xylidine, etc., are increasingly expanding.

Such anilines as mentioned above have heretofore been prepared by processes involving ① catalytic reduction of aromatic nitro compounds, ② reaction of aromatic halides with ammonia water at high temperatures under pressure, or ③ reaction of phenols with ammonia.

In the above-mentioned process ① involving the use of the nitrocompounds, however, there is involved such problem that because of necessitating large amounts of sulfuric acid and nitric acid as nitration agents, large amounts of alkali substances such as sodium hydroxide are needed in the neutralization step and, moreover, large amounts of waste water containing salts in high concentrations are produced. In addition thereto, there is involved such problem that, as pointed out in Japanese Patent L-O-P Pubin. No.67229/1973, nitrogen oxide gas is generated during the course of operation to prepare the nitro compounds, whereby air pollution with said nitrogen oxide gas is brought about.

The process ② relying on the use of aromatic halides has such a fundamental problem that expensive corrosion-resistant equipments should be used for practicing said process because chlorine that is very high in corrosive properties has to be used therefor. Notwithstanding that the reaction of chlorobenzene with ammonia is carried out under high temperature and pressure circumstances, moreover, it has been pointed out that desired anilines are obtained in low yields, and under the present conditions this process is not practically applied to aromatic halides except for p-nitrochlorobenzene having a nitro group at the para-position.

From the reasons cited above, the process ③ relying on reaction of phenols with ammonia has become of major interest lately, and at present this process is coming to take a leading figure in the processes for preparation of anilines. That is, according to this process the desired anilines can be prepared by simply passing phenols and ammonia through fixed bed catalysts, and hence there are observed such excellent advantages that no problem of air pollution due to nitrogen oxide gas arises, no large amount of waste water are produced and the operational process can be markedly simplified.

As a typical example of the preparation of anilines by reaction of phenols with ammonia, there may be mentioned a process as disclosed in Japanese Patent Publication No.23571/1967. According to the process for preparing aminobenzene disclosed in the above-cited patent publication, aminobenzene such as aniline is prepared by reacting hydroxybenzene such as phenol with an amination agent at a temperature of 300°–600° C. by using a catalyst selected from the group consisting of silica-alumina, zirconia-alumina, titania-alumina, zirconia-silica phosphate and tungsten oxide. In this connection, this patent publication teaches that because of low activity exhibited in such amination reaction as mentioned above, weakly acidic solid acid such as commercially available-alumina catalyst is insufficient as a catalyst for use in said amination reaction, whereas silica-alumina catalyst which is a strongly acidic solid acid comprising silica or alumina in an amount of 10–20% of the weight of the catalyst is particularly excellent as a catalyst for use in the amination reaction.

However, where the strongly acidic solid acid catalyst such as silica-alumina catalyst is used in the amination reaction, there is such problem that undesirable side reaction such as decomposition of aniline being formed or formation of resinous substance as by product takes place though the initial activity of the amination reaction is high. Furthermore, there is encountered such a fatal problem that deterioration of the catalyst rapidly proceeds when such resinous substance attaches to the catalyst surface to cover the active site of the catalyst. On that account, it was necessary to effect frequently a catalyst regeneration operation.

An attempt to solve such problems as mentioned above is disclosed in Japanese Patent L-O-P Publn. No.67229/1973, which teaches that the reaction of phenols with an amination agent is carried out by using a catalyst which is weak in acid strength in comparison with the above-mentioned silica-alumina catalyst (pKa −8.0), that is, titania-zirconia and titania-silica catalysts which are solid acid catalyst, the acid value of which is distributed in the range of from −5.6 to −3.0 in terms of pKa. Even when such catalysts are used, however, the reaction temperature employed must be elevated to such high temperature as ranging from 400° to 500° C. in order to accomplish an effective amination reaction. At this elevated temperature, however, decomposition of ammonia which is the amination agent, that is, $NH_3 \rightarrow \frac{1}{2}N_2 + 3/2H_2$, is accelerated, whereby deterioration of the reaction apparatus due to nascent nitrogen at the time when it is generated. Thus, the process thus taught still involves such problem that a lifetime of the reaction apparatus used therefor is markedly shortened.

Furthermore, a sharp lowering of catalyst activity is observed during operation continued for only about 40 hours, and it is difficult to carry out this process on an industrial scale.

Besides the foregoing, Japanese Patent L-O-P Publn. No.23052/1971 discloses a process for amination of phenols using catalysts comprising a combination of dehydrated solid acid catalysts and hydrogenated catalysts, and Japanese Patent L-O-P publn. No.23053/1971 also discloses the amination of phenols by using catalysis comprising a combination of alumina or silica and an oxide selected from the group consisting of magnesia, boria and thoria. In each of these processes, however, an improvement made is barely prolongation of duration of the catalyst activity to 50–100 hours, and no solution of the catalyst deterioration problem is made at all.

In the manner now described, the known processes for the preparation of anilines by amination of phenols all require the employment of high temperature higher than 400° C. in order to carry out the amination reaction efficiently. On that account, there were such fatal problems that the apparatus used therefor deteriorates due to nascent nitrogen generated by the decomposition of ammonia which is the amination agent, and that the catalyst regeneration operation is frequently necessary because the catalyst deterioration takes place due to contamination of the catalyst surface with resinous substance formed by decomposition of anilines being formed, deposition on the catalyst surface of carbonaceous substance formed by decomposition of organic materials or the like, thereby the catalyst activity decreases in a short period of time.

OBJECT OF THE INVENTION

The present invention is intended to solve the above-mentioned problems associated with the prior art, and an object of the invention is to provide a process for preparing anilines by reacting phenols with an amination agent, by which the desired anilines are obtained in high yield and high selectivity without causing deterioration of catalytic activity by virtue of using specific catalysts of the present invention even when the reaction is carried out at a temperature lower than those employed in the prior art processes.

Another object of the present invention is to provide alumina catalysts which are preferably used in the reaction to prepare anilines by reacting phenols with an amination agent, by the use of which the desired anilines are obtained in high yields and high selectivity even when said reaction is effected at a temperature lower than those employed in the prior art processes, and which are capable of retaining their catalyst activity over a long period of time, and a process for preparing said alumina catalysts.

SUMMARY OF THE INVENTION

The process for preparing anilines of the present invention, which comprises reacting phenols with an amination agent, is characterized in that the phenol is reacted with the amination agent in the presence of a low alkali and weakly acidic alumina catalyst having the alkali metal oxide content of less than 0.5% by weight, which is obtained by firing an alumina catalyst containing in a dry state more than 80% by weight of alumina and less than 20% by weight of silica at a temperature of 600°–900° C. followed by acid treatment.

The alumina catalysts of the present invention are characterized by containing in a dry state more than 80% by weight of alumina and less than 20% by weight of silica, the alkali metal content of which is less than 0.5% by weight and pKa of which as measured by Hammett's indicator is from −3.0 to +6.8.

The process for preparing the alumina catalysts of the present invention is characterized by firing an alumina catalyst containing in a dry state more than of alumina and less than 20% by weight of silica at a temperature of 600°–900° C. followed by acid treatment, and regulating the resulting catalyst so that its alkali metal oxide content is less than 0.5% by weight and its pKa as measured by Hammett's indicator is from −3.0 to +6.8.

In the process for preparing anilines according to the present invention, since phenols are reacted with an amination agent in the presence of a specific alumina catalyst having the alkali metal oxide content of less than 0.5% by weight, which is obtained by firing an alumina catalyst containing in a dry state more than 80% by weight of alumina and less than 20% by weight of silica at a temperature of 600°–900° C. followed by acid treatment, there are obtained such excellent effects that the desired anilines can be prepared in high yields and high selectivity even when the reaction is carried out at a temperature lower than those employed in the prior art processes and, moreover, that the catalyst used is capable of sustaining its catalyst activity over a long period of time.

The alumina catalysts obtained by the process of the present invention have such a low alkali metal oxide content of less than 0.5% by weight and are low alkali weakly acidic catalysts having such a large pKa of from −3.0 to +6.8. When the present alumina catalysts as mentioned above are used in the preparation of anilines by reacting phenols with an amination agent, there are obtained such excellent effects that the desired anilines are obtained in high yields and high selectivity even when the reaction is effected at a temperature lower than those employed in the prior art processes, and that a high catalyst activity can be sustained over a long period of time.

BRIEF DESCRIPTION OF THE DRAWING

The accompanying drawing shows cumulative pore distribution curves obtained in Example 1 and Comparative Examples 1–2, respectively, provided that the cumulative pore distribution curves are shown by assuming 0 the sum of volumes of pores having a pore diameter of larger than 1000 Å.

DETAILED DESCRIPTION OF THE INVENTION

The process for preparing anilines according to the present invention, the catalysts used in the reaction of said process and a process for preparing said catalysts in accordance with the invention are illustrated below in more detail.

Phenols

In the present invention, the desired anilines are prepared by reacting phenols with an amination agent. Usable phenols as starting materials include phenol, cresol or o-, m- or p-isomers of ethylphenol or isopropylphenol, and alkyl phenols having at least one alkyl substituent, such as dimethylphenol, methylethylphenol, methylisopropylphenol, methylbutylphenol, diethylphenol, ethylbutylphenol, diisopropylphenol, isopropylbutylphenol, and dibutylphenol. Furthermore, mixtures of phenols and alkyl phenols can also be used, and said mixture may have any percentages composition.

Of these phenols as exemplified above, particularly preferred is phenol.

Amination agent

Amination agents which are used in the reaction with such phenols as mentioned above include ammonia, ammonia generating compounds or organic amines. The ammonia generating compounds are inorganic compounds which generate ammonia gas on thermal decomposition thereof. Such inorganic compounds include ammonium carbonate, ammonium sulfate, etc. The organic amines include methylamine, ethylamine, n-propylamine, dimethylamine, diethylamine, diisopropylamine, methylethylamine, cyclohexylamine, aminopyridine, aniline, methylaniline, ethylaniline, n-propylaniline, isopropylaniline, dimethylaniline, diethylaniline, dipropylaniline, methylethylaniline, methylpropylanlline, etc. Of these amination agents exemplified above, particularly preferred is ammonia.

Catalyst

In the present invention, the aforementioned phenols are reacted with the above-exemplified amination agents in the presence of a low alkali and weakly acidic alumina catalyst having the alkali metal oxide content of less than 0.5% by weight, which Is obtained by firing an alumina catalyst containing in a dry state more than 80% by weight of alumina and less than 20% by weight of silica at a temperature of 600°–900° C. followed by acid treatment.

The untreated alumina catalyst containing in a dry state more than 80% by weight of alumina and less than 20% by weight of silica, which is used in the present invention in the manner as mentioned above, is well known. Such untreated alumina catalyst includes H-151 and H-152, products produced and sold by Alcoa Co. The untreated alumina catalyst used has a specific surface area of more than 100 $m^2/g$ and usually contains less than 10% by weight of alkali metal oxides.

Such untreated alumina catalysts are fired at a temperature of 600°–900° C., preferably 700°–800° C. The firing is usually carried out in air atmosphere or nitrogen atmosphere, but is preferably carried out in air atmosphere.

In this connection, it is not preferable to employ the firing temperature of less than 600° C. as no low alkali and weakly acidic alumina catalyst having a desired catalyst activity can be obtained. It is also not preferable to employ the firing temperature exceeding 900° C. as the alumina catalyst being fired is liable to sintering, whereby a sharp decrease in specific surface area is observed and, as a matter of more importance, alumina structure of the catalyst changes from γ (gamma) form to α (alpha) form which does not exhibit any amination activity at all, with the result that the catalyst activity of the alumina catalyst thus treated markedly decreases.

The firing time employed in firing the aforesaid untreated alumina catalyst is 5–100 hours, preferably 5–50 hours.

The thus fired untreated alumina catalyst according to the above-mentioned procedure is then subjected to acid treatment. Acids used in this acid treatment include organic acids such as acetic acid, oxalic acid, citric acid, etc., and inorganic acids such as hydrochloric acid, sulfuric acid, boric acid, phosphoric acid etc. Of these acids, particularly preferred is acetic acid.

In the acid treatment of the thus fired alumina catalyst, a concentration of the acid used, treatment time and treatment temperature are so selected that the alkali metal oxide content in the alumina catalyst is decreased to less than 0.5% by weight.

In practicing the above-mentioned acid treatment, the organic acid may be used, as it is, but it is preferable to use said acid in the form of aqueous solution in the same manner as in the case of the inorganic acid. Where the acid is used in the form of aqueous solution, it is preferable to use the aqueous solution having a concentration of about 2–20% by weight of the acid. When the alumina catalyst is treated with an aqueous acid solution having an excessively high concentration, salts resulting from neutralization reaction or the acid remain attached to the catalyst, and it is not preferable to use the thus treated catalyst, as it is, in the reaction of phenols with an amination agent as the catalyst surface is sometimes contaminated with such salts or acid.

The acid treatment of the alumina catalyst may be carried out by either batchwise or continuous process. When this treatment is carried out by the batchwise process, the fire treated alumina catalyst is immersed in an aqueous acid solution having the aforesaid concentration, and in this case it is preferable to use the acid having such a concentration that some free acid remains in the aqueous solution. When the acid treatment Is carried out by the continuous process, on one hand, the fire treated alumina catalyst as aforesaid is preferably packed into an amination reaction apparatus, an aqueous acid solution is continuously passed through said apparatus, and the aqueous acid solution leaving the catalyst layer is again circulated to the catalyst layer. When the acid is deficient in amount, it is preferable to supply the acid, as it is, or in the form of aqueous solution to the apparatus through the middle part of the circulation line.

Although no particular limitation is placed on the temperature conditions employed in the acid treatment step, the temperature employed is preferably 20°–50° C.

The alumina catalyst subjected to firing treatment and then to acid treatment, prior to using it in the reaction of phenols with an amination agent, is preferably subjected to water-washing, drying and firing steps in that order, but these steps are not always necessary.

In actual practice, since the reaction of phenols with an amination agent is carried out at high temperatures, it follows that the drying of the catalyst is effected at the time of initiation of the reaction, but speaking from a practical standpoint, the catalyst subjected to water-washing, drying and firing steps is longer in catalyst life than the catalyst not subjected to these steps, and the formation of tarry products as by-products can be inhibited. The water-washing step is effected in order to remove the acid and salts resulting from neutralization which attached to the catalyst surface when the catalyst is subjected to acid treatment. Accordingly, when the acid treatment is carried out by using a diluted aqueous acid solution, the water-washing step is not always necessary. Furthermore, no particular limitation is placed on the drying and firing steps, but it is preferable to carry out at 400°–600° C., particularly 450°–550° C. By virtue of carrying out the heat treatment of the acid treated catalyst, carbulation of the residual acid can be prevented by combustion removal of the organic acid used, and the effect of inhibiting side reactions at the time of the reaction of phenols with an amination agent becomes large.

In comparison with untreated alumina catalysts, the alumina catalyst thus subjected to firing treatment and acid treatment has a small content of alkali metal oxide and, in addition thereto, the pore distribution of the treated alumina catalyst as measured by the mercury injection method is apparently different from those of the untreated alumina catalyst. That is, the alumina catalyst treated in accordance with the present invention has a large volume of pores of 100 Å–60 Å as measured by the mercury injection method such as 0.18 cc/g or more, preferably 0.20 cc/g or more.

The pore distribution of untreated alumina catalysts and that of the alumina catalyst treated in accordance with the present invention are shown In FIG. 1. As can be seen from this FIG. 1, the distribution of pores of 100 Å–60 Å of the present treated alumina catalyst is sharp and the volume of 100 Å–60 Å pores is very large such as about 0.26 cc/g, whereas the distribution or pores of 100 Å–60 Å of the untreated alumina catalyst is not sharp and the volume of pores of 100 Å–80 Å is very small such as about 0.075 cc/g. Furthermore, the pore distribution of the alumina catalyst is also shown, said alumina catalyst being obtained by subjecting the aforesaid untreated alumina catalyst to acid treatment, followed by firing. The pore distribution of this alumina catalyst is not sharp, and the volume of pores of 100 Å–60 Å thereof is 0.102 cc/g. This value is considerably small as compared with the alumina catalyst treated in accordance with the present invention.

Furthermore, in the alumina catalyst treated in accordance with the present invention, the acid strength distribution as measured by means of Hammett's indicator ranges from −3.0 to +6.8 in terms of pKa. This value, in comparison with the catalysts for preparing anilines disclosed in the aforesaid Japanese Patent Publn. No.23571/1967 and Japanese Patent L-O-P Publn. No.67229/1970, shows that the present alumina catalyst is considerably weakly acidic as compared with the prior art catalysts.

When the alumina catalyst of the present invention thus prepared is used in the reaction of phenols with an amination agent, the selectivity and yield of the desired anilines are markedly improved. The reason therefor is presumed as in the following. That is, it is considerered that because the present alumina catalyst is sharp in the pore distribution of pores of less than 100 Å and, moreover, the pore volume of pores of less than 100 Å is large, diffusion rate of the reactants within pores increases and useful catalyst coefficient improves, and hence the catalyst activity becomes high and the selectivity and yield of the desired aniline are markedly improved. Furthermore, it is considered that because the pore volume of pores of less than 100 Å is large, diffusion of high boiling substances which will form the cause of lowering the catalyst activity from the inside of pores to the outside thereof becomes easy, and on that account it becomes possible to restrain accumulation inside the pores of the high boiling substances and consequently a high catalyst activity can be maintained over a long period of time.

In accordance with the process of the present invention as illustrated above, it is possible to minimize the reaction space or volume necessary for preparing a given amount of anilines because the catalysts high in activity are available, and there is observed such effect that the reaction temperature required for attaining the desired amount of product anilines can be lowered. Thus, there are observed such excellent effects that because of the possibility of employing such low reaction temperature as mentioned above, the selectivity of the product anilines becomes large and formation of carbonaceous substances due to decomposition of aniline or formation of resinous substances can be markedly restrained and accordingly the catalyst life is markedly prolonged.

Reaction conditions

In the present invention, phenols are reacted with an amination agent in the presence of a low alkali and weakly acidic alumina catalyst prepared in the manner now described, and the reaction conditions employed in that case are almost the same as the well-known conditions.

For instance, the reaction temperature employed in the present invention is about 300°–600° C., preferably 300°–400° C., which are almost the same as the temperatures employed in the well-known conditions. In the present invention, however, the reaction can be carried out in the lower temperature region. The reaction may be effected either at ordinary pressure or under pressure, and the pressure employed is preferably about 5–50 atmospheres. Furthermore, the ammonia/phenols molar ratio is about 1–40, preferably about 3–30.

The amination reaction of phenols in accordance with the present invention may be effected in either vapor phase or liquid phase. In order to obtain the desired anilines in high selectivity and high yields, it is preferable to carry out the reaction in vapor phase. Furthermore, the reaction of the present invention may be carried out either by continuous or batchwise process, but in order to prepare the desired anilines in large quantity and cheaply on a commercial scale, it is preferable to adopt the continuous process.

In the present invention, a liquid space velocity (LHSV) employed ranges form 0.01–0.1 $hr^{-1}$, preferably from 0.02–0.06 $hr^{-1}$. This liquid space velocity is a value obtained by dividing a feed volume (1/hr) of phenols per unit time by a catalyst volume (1) packed into a reaction column or pipe.

The reaction of phenols with an amination agent of the present invention, when carried out by the continuous phase reaction, is illustrated below in detail. A mixture of liquid phenols, together with liquid ammonia, is vaporized, or they are separately vaporized and then mixed together, and the heated phenols are further vaporized by the superheated ammonia, and the mixture obtained is fed into a reactor charged with the catalyst and maintained at the above-mentioned pressure and reaction temperature. The pressure of reaction mixture withdrawn from the reactor is restored to ordinary pressure and the reaction mixture is cooled. This reaction mixture contains ammonia in a considerable proportion, and hence the ammonia is separated by fractional distillation.

Unreacted ammonia separated from the reaction mixture is recycled for use. On one hand, the reaction product liquid from which the ammonia has been removed is fed to the subsequent dehydration distillation step, followed by separation and purification of anilines as formed, then the purified anilines are recovered. On the other hand, unreacted phenols recovered are recycled to the reactor for reuse.

EFFECT OF THE INVENTION

In the process for preparing anilines by reacting phenols with an amination agent, since a specific alumina catalyst having the alkali metal oxide content of less than 0.5% by weight, which is obtained by firing an alumina catalyst containing in a dry state more than by weight of alumina and less than 20% by weight of silica at a temperature of 600°–900° C., is used in the reaction, there are obtained such excellent effects that the desired anilines can be prepared in high yields and high selectivity even when the reaction is carried out at temperature lower than those employed in the case of conventionally known catalysts and, moreover, a high catalyst activity can be maintained over a long period of time.

The present invention is illustrated below with reference to examples, but it should be understood that the invention is in no way limited to these examples.

EXAMPLE 1

A muffle furnace was loaded with an alumina catalyst produced by Alcoa Co.(an alumina catalyst sold by Mortmura Shoji K.K. an agent for Alcoa in Japan under a trade name of H-152, $Al_2O_3$:80.6%, $SiO_2$: 9.9%, $Fe_2O_3$:0.03%, $TiO_2$: 0.003%, CaO:0.03%, MgO:0.004%, $Na_2O$:5.4%, and $K_2O$:0.07%, a specific surface area of 176m²/g by BET method, a cumulative pore volume of pores having a pore diameter of larger than 60 Å being 0.165 cc/g by the mercury injection method, the sum of pore volumes of pores of a pore diameter of less than 100 Å up to 60 Å being 0.079 cc/g, an average pore diameter being 191 Å, a total acid amount by Hammet's indicator being 0.26 meq/g, and an acid amount in a weakly acidic region of pKa of from +6.8 up to +1.5 being 0.04 meq/g), and firing of the catalyst was effected in air atmosphere at 700° C. for 5 hours.

After the 5-hour firing, the heated catalyst was cooled to room temperature, and then 900ml out of the thus treated alumina was packed into a glass tube, and nitrogen gas saturated with water under room temperature was continuously fed to the glass tube to swell the alumina. Subsequently, 1.5l of 10 w/v % aqueous acetic acid solution was circulated with a pump through the catalyst layer at a rate of about 3l/hr. After initiation of the circulation, the acetic acid concentration in the circulating water reached equilibrium in about 8 hours. Thereafter, the pump was suspended to operate and the aqueous acetic acid solution was withdrawn from the catalyst layer, and then distilled water was continuously passed through the catalyst layer by the pump to effect removal by rinsing of neutralized salt (sodium acetate) formed by acetic acid treatment.

Subsequently, the catalyst thus treated was dried by circulation of hot air, and finally fired at 500° C. for 5 hours.

In the catalyst thus prepared, a specific surface area as measured by BET method was 136 m²/g, a cumulative pore volume of pores having a pore diameter of larger than 60 Å as measured by the mercury injection method, was 0.410 cc/g, an average pore diameter of 99 Å, and in the acid strength distribution as measured by Hammett's indicator, the acid amount in a weakly acidic region ranging from pKa +1.5 to 6.8 was 0.10 meq/g based on the total acid amount of 0.34 meq/g. The sodium oxide content was less than 0.5% by weight. A pore volume of pores having a pore diameter of more than 60 Å was 0.411 cc/g, and the sum of pore volumes of pores having a pore diameter of less than 100 Å and up to 60 Å was 0.262 cc/g.

This low alkali and weakly acidic alumina catalyst was packed in an amount of 660 ml into a central portion of a reaction tube made of SUS 321 having an inside diameter of 25.0 mm and a length of 2 m, and the reactor was heated in an electric furnace while passing ammonia gas there therethrough, and then elevated up to the predetermined temperature. The feeding of phenol was effected after reaching the predetermined temperature by using a micropump. The reaction was carried out at a pressure of 15 Kg/cm² G in the presence of ammonia. The feed rate of phenol was 0.045 $hr^{-1}$ in terms of LHSV, and the ammonia phenol molar ratio was 15.

A vapor liquid separator was placed at the outlet of the reactor and the reaction product liquid was collected. The reaction product liquid contained water formed by amination reaction and assumed 2-liquid phase, and hence a given volume of the liquid was subjected to sampling while stirring to which a given volume of methanol, forming a homogeneous phase. 1 μl of the liquid thus treated was injected into a gas chromatography apparatus (column:sp-1000/chromosolp WAW), and the determination was effected by the correction surface percentage method.

The composition of the reaction product obtained, and conversion and selectivity are shown in the following table.

$$\text{Conversion (\%)} = \frac{\text{Number of moles of phenols reacted in unit time}}{\text{Number of moles of phenols fed in unit time}} \times 100$$

$$\text{Selectivity (\%)} = \frac{\text{Number of moles of anilines formed in unit time}}{\text{Number of moles of phenols reacted in unit time}} \times 100$$

The amination activity of phenol at each reaction temperature was shown in terms of conversion and selectivity in Table 1. A continuous operation was effected for about 1000 hours under the conditions of the reaction temperature of 380° C., LHSV of 0.045 $hr^{-1}$, reaction pressure of 15 Kg/cm G. and ammonia/phenol molar ratio of 15, whereupon no decrease in phenol conversion and aniline selectivity was observed at all.

EXAMPLE 2

Example 1 was repeated except that the alumina catalyst (H-152, a product of alcoa Co.) was fired for 10 hours at 700° C. The low alkali and weakly acidic alumina catalyst obtained had a specific surface area of 134 m²/g as measured by BET method, a volume (cumulative pore volume) of pores having a pore diameter of more than 60 Å was 0.439 cc/g as measured by the mercury injection method, an average pore diameter of 101 Å, and an acid strength distribution as measured by Hammett's indicator which shows an acid amount in a weakly acidic region ranging from pKa +1.5 to +6.8 of 0.08 meq/g based on the total acid amount of 0.32 meq/g. Of the cumulative pore volume of 0.439 cc/g, the sum of pore volumes of pores having a pore diameter of less than 100 Å and up to 60 Å was 0.288 cc/g. The sodium oxide content was less than 0.5% by weight.

The amination activity test results of phenol obtained by using this catalyst with the same reaction apparatus as in Example 1 under the same reaction conditions are shown in Table 1. The continuous operation was conducted for about 1000 hours under the conditions described in Example 1, whereupon no decrease in phenol conversion and aniline selectivity was observed at all.

EXAMPLE 3

Example 1 was repeated except that the alumina catalyst (H-152) was fired for 20 hours at 700° C., (provided that the firing was effected in air atmosphere). The low alkali and weakly acidic alumina catalyst obtained had a specific surface area of 118 m²/g as measured by BET method, a volume of pores having a pore diameter of more than 60A being 0.459cc/g as measured by the mercury injection method, an average pore diameter of 113 Å, and an acid strength distribution as measured by Hammett's indicator, which shows an acid amount in a weakly acidic region of from pKa +1.5 up to +6.8 being 0.11 meq/g based on the total acid amount of 0.31 meq/g. The sodium oxide content was less than 0.5% by weight.

Of the pore volume of 0.461 cc/g, the sum of pore volumes of pores having a pore diameter of less than 100 Å up to 60 Å was 0.236 cc/g.

The amination activity test results of phenol obtained by using this catalyst and the same reaction apparatus as in Example 1 under the same reaction conditions are shown in Table 1.

The continuous operation was conducted for about 1000 hours under the reaction conditions described in Example 1, whereupon no decrease in phenol conversion and aniline selectivity was observed at all in the same manner as in Example 1.

EXAMPLE 4

Example 1 was repeated except that the alumina catalyst (H-152) was fired for 40 hours at 700° C., (provided that the firing was effected in air atmosphere). The low alkali and weakly acidic alumina catalyst obtained had a volume of pores having a pore diameter of more than 60 Å of 0.465 cc/g as measured by the mercury injection method, an average pore diameter of 115 Å. The sodium oxide content was less than 0.5% by weight.

Of the pore volume of 0.466 cc/g, the sum of pore volumes of pores having a pore diameter of less than 100 Å up to 60 Å was 0.2400 c/g.

The amination activity test results of phenol obtained by using this catalyst and the same reaction apparatus as in Example 1 under the same reaction conditions as in Example 1 are shown in Table 1.

EXAMPLE 5

Example 1 was repeated except that the alumina catalyst (H-152) was fired for 5 hours at 800° C. The low alkali and weakly acidic alumina catalyst obtained had a specific surface area of 118 $m^2/g$ as measured by BET method, a volume of pores (cumulative pore volume) having a pore diameter of more than 60 Å of 0.466 cc/g, as measured by the mercury injection method, an average pore diameter of 115 Å, and an acid strength distribution as measured by Hammett's indicator, which shows that an acid amount in a weakly acidic region ranging from pKa +1.5 up to +6.8 was 0.11 meq/g based on the total acid amount of 0.31 meq/g. Of the cumulative pore volume of 0.466 cc/g, the sum of pore volumes of pores having a pore diameter of less than 100 Å up to 60 Å was 0.207 cc/g. The sodium oxide content was less than 0.5% by weight.

The amination activity test results of phenol obtained by using this catalyst and the same reaction apparatus as in Example 1 under the same reaction conditions as in Example 1 are shown in Table 1.

EXAMPLE 6

Example 1 was repeated except that the alumina catalyst (H-152) was fired for 10 hours at 800° C. The low alkali and weakly acidic alumina catalyst obtained had a specific surface area of 110 $m^2/g$ as measured by BET method, a volume of pores (cumulative pore volume) of pores having a pore diameter of more than 60 Å of 0.365 cc/g, as measured by the mercury injection method, an average pore diameter of 90 Å, and an acid strength distribution as measured by Hammatt's indicator, which shows that an acid amount in a weakly acidic region ranging from pKa +1.5 up to +6.8 was 0.13 meq/g based on the total acid amount of 0.33 meq/g. Of the cumulative pore volume of 0.365 cc/g, the sum of pore volumes of pores having a pore diameter of less than 100 Å up to 60 Å was 0.264 cc/g.

The amination activity test results of phenol obtained by using this catalyst and the same reaction apparatus as in Example 1 under the same reaction conditions as in Example 1 are shown in Table 1.

EXAMPLE 7

Example 1 was repeated except that the alumina catalyst (H-152) was fired for 20 hours at 600° C. The low alkali and weakly acidic alumina catalyst obtained had a volume of pores (cumulative pore volume) having a pore OF more than 60 Å of 0.407 cc/g, as measured by the mercury injection method, an average pore diameter of 102 Å. Of the cumulative pore volume of 0.407 cc/g, the sum of pore volumes of pores having a pore diameter of less than 100 Å up to 60 Å was 0.253 cc/g.

The amination activity test results of phenol obtained by using this catalyst and the same reaction apparatus as in Example 1 under the same reaction conditions as in Example 1 are shown in Table 1.

Comparative Example 1

Into the reaction apparatus as described in Example 1 was packed in an amount of 660 cc an alumina catalyst (H-152) sold by Alcoa co., as it was, heated in an electric furnace while passing ammonia gas therethrough and elevated in temperature up to the predetermined temperature. After reaching the predetermined temperature, phenol was fed by a micropump to the reactor. The reaction was carried out under a pressure of 15 $Kg/cm^2G$ in the presence of ammonia.

The feed rate of phenol was 0.045 hr in terms of LHSV, and the ammonia/phenol molar ratio was 15. Phenol conversion and aniline selectivity obtained at varying reaction temperatures are shown in Table 1.

Comparative Example 2

900 ml of the alumina catalyst (H-152), as it was, was packed into a glass tube, and nitrogen gas saturated with water under room temperature was continuously passed through the catalyst layer to swell the catalyst. Subsequently, 1.5 l of 10 w/v % aqueous acetic solution was circulated using a pump through the catalyst layer at a rate of about 3 l/hr. After initiation of the circulation, the acetic acid concentration in the circulating water reached equilibrium in about 8 hours. The pump was suspended to operate, after withdrawing of the aqueous acetic solution, distilled water was continuously passed by the pump through the catalyst layer to remove by rinsing neutralized salt (sodium acetate-)formed by acetic acid treatment.

After water-washing, the catalyst was dried by circulating hot air, and finally fired in a muffle furnace for 5 hours at 700° C.

The low alkali and weakly acidic alumina catalyst thus prepared had a specific surface area of 167 $m^2/g$ as measured by BET method, a volume of pores (cumulative pore volume) having a pore diameter of more than 60 Å of 0.383 cc/g as measured by the mercury injection method, an average pore diameter of 125 Å, and an acid strength distribution as measured by Hammett's indicator, which shows that an acid amount in a weakly acidic region ranging from pKa +1.5 up to +6.8 was 0.10 meq/g based on the total acid amount of 0.38 meq/g. Of the cumulative pore volume of 0.383 cc/g, the sum of pore volumes of pores having a pore diameter of less than 100 Å up to 60 Å was 0.170 cc/g.

The amination activity test results of phenol obtained by using this catalyst and the some reaction apparatus as in Example 1 under the same reaction conditions as in Example 1 are shown in Table 1.

Comparative Example 3

Into a glass tube was packed the alumina catalyst (H-152), as it was, and subjected to acetic acid treatment described in Comparative Example 2. After the acetic acid treatment and subsequent water-washing, the catalyst thus treated was dried by circulating hot air and finally fired in a muffle furnace for 5 hours at 500° C.

The low alkali and weakly acidic alumina catalyst thus prepared had a specific surface area of 183 m$^2$/g as measured by BET method, a volume of pores (cumulative pore volume) having a pore diameter of more than 60 Å of 0.286 cc/g as measured by the mercury injection method, an average pore diameter of 127 Å, and an acid strength distribution as measured by Hammett's indicator, which shows that an acid amount in a weakly acidic region ranging from pKa +6.8 to +1.5 was 0.13 meq/g based on the total acid amount of 0.41 meq/g. Of the cumulative pore volume of 0.286 cc/g, the sum of pore volumes of pores having a pore diameter of less than 100 Å up to 60 Å was 0.106 cc/g.

The amination activity test results of phenol obtained by using this catalyst and the same reaction apparatus as in Example 1 under the same reaction conditions as in Example 1 are shown in Table 1.

Comparative Example 4

Into a muffle furnace was fed 1000 ml of the alumina catalyst H-152, as it was, and fired for 5 hours at 700° C., in air atmosphere. The alumina catalyst thus fired had a cumulative pore volume of pores having a pore diameter of more than 60 Å of 0.345 cc/g as measured by the mercury injection method and an average pore diameter of 94 Å. 5 hours after the firing, the alumina catalyst was cooled to room temperature. Into the same reactor as in Example 1 was packed 660 ml of the thus fired alumina catalyst.

In accordance with the reaction conditions as described in Example 1, the activity test of this alumina catalyst was conducted. The results obtained are shown in Table 1.

What is claimed is:

1. A process for preparing an aniline compound in improved yield by reaction of a phenol compound with an amination agent, characterized by reacting the phenol compound with the amination agent in the presence of low alkali and weakly acidic alumina catalyst having an alkali metal oxide content of less than 0.5% by weight, said alumina catalyst being obtained by firing an alumina catalyst containing in a dry state more than 80% by weight of alumina and less than 20% by weight of silica at a temperature of 700°–900° C. following by acid treatment whereby the yield of aniline compound is improved as a result of said firing and acid treatment.

2. The process as claimed in claim 1 wherein the phenol compounds is phenol and the amination agent is ammonia.

3. The process as claimed in claim 1 wherein the alumina catalyst is further characterized by a pKa of from −3.0 to +6.8 as measured by Hammett's indicator.

4. The process as claimed in claim 3 wherein the alumina catalyst is further characterized by a pore volume for pores of from 100 Å to 60 Å, as measured by the mercury injection method, of at least 0.18 cc/g.

5. The process as claimed in claim 1 wherein the alumina catalyst is further characterized by a pore volume for pores of from 100 Å to 60 Å, as measured by the mercury injection method, of at least 0.18 cc/g.

6. The process as claimed in claim 3 wherein the alumina catalyst is further characterized by a pore volume for pores of from 100 Å to 60 Å, as measured by the mercury injection method, of at least 0.20 cc/g.

7. The process as claimed in claim 1 wherein the alumina catalyst is further characterized by a pore volume for pores of from 100 Å to 60 Å, as measured by the mercury injection method, of at least 0.20 cc/g.

8. A process for preparing an aniline compound in improved yield by reaction of a phenol compound with an amination agent which comprises firing an alumina catalyst containing in a dry state more than 80% by weight of alumina and less than 20% by weight of silica at a tempera-

TABLE 1

Result on test of amination activity of phenol
Conditions of reaction: Reaction presure = 15 Kg/cm$^2$G, LHSV (hr$^{-1}$) = 0.045, NH$_3$/phenol (molar ratio) = 15

|  | Examples | | | | | | | Comparative Examples | | | |
| --- | --- | --- | --- | --- | --- | --- | --- | --- | --- | --- | --- |
|  | 1 | 2 | 3 | 4 | 5 | 6 | 7 | 1 | 2 | 3 | 4 |
| Phenol. conversion | | | | | | | | | | | |
| 395° C. |  |  |  |  |  |  |  | 21.0 |  | 99.4 | 40.2 |
| 390° C. | 99.7 |  |  |  |  | 99.7 |  |  | 99.3 | 98.1 |  |
| 380° C. | 99.0 | 99.7 | 99.7 | 99.4 | 99.6 | 99.7 | 99.4 |  | 86.4 | 84.8 |  |
| 375° C. |  | 98.9 | 99.1 | 98.0 | 98.1 | 98.2 | 96.3 |  |  |  |  |
| 370° C. | 85.8 | 90.2 | 92.0 | 92.3 | 89.5 | 88.2 | 87.6 |  |  |  |  |
| Aniline Selectivity | | | | | | | | | | | |
| 395° C. |  |  |  |  |  |  |  | 99.2 |  | 98.2 | 98.9 |
| 390° C. | 98.3 |  |  |  |  | 98.6 |  |  | 98.2 | 98.3 |  |
| 380° C. | 98.5 | 98.6 | 98.5 | 98.5 | 98.7 | 98.8 | 98.5 |  | 98.9 | 98.8 |  |
| 375° C. |  | 98.8 | 98.7 | 98.8 | 98.8 | 98.9 | 98.7 |  |  |  |  |
| 370° C. | 98.9 | 98.9 | 98.9 | 98.8 | 99.0 | 99.1 | 98.9 |  |  |  |  |

From Table 1, it is understood that a conversion of phenol was high and, moreover, a selectivity of aniline was favorable when the process for preparing anilines of the present invention was carried out.

ture of from 700° to 900° C., acid-treating the fired alumina catalyst to reduce the alkali metal oxide content thereof to less than 0.5% by weight and obtaining a pKa of from −3.0 to +6.8 as measured by Hammett's indicator, and reacting the phenol compound with the amination agent in the presence of the resulting low alkali and weakly acidic alumina catalyst whereby the yield of aniline compound is improved as a result of said firing and acid treatment.

9. The process of claim 1 wherein the alumina catalyst is fired at a temperature of about 700° C.

10. The process of claim 8 wherein the alumina catalyst is fired at a temperature of about 700° C.

11. The process of claim 1 wherein following the treatment of the alumina catalyst, the catalyst is water-washed, dried and fired at a temperature of from about 450° C. to about 550° C.

12. The process of claim 8 wherein following the treatment of the alumina catalyst, the catalyst is water-washed, dried and fired at a temperature of from about 450° C. to about 550° C.

13. The process of claim 1 wherein the reaction between the phenol compound and amination reaction in the presence of the alumina catalyst is carried out at a temperature of from 370° C. to 390° C.

14. The process of claim 8 wherein the reaction between the phenol compound and amination reaction in the presence of the alumina catalyst is carried out at a temperature of from 370° C. to 390° C.

* * * * *